(12) United States Patent
Liu

(10) Patent No.: US 12,193,760 B2
(45) Date of Patent: Jan. 14, 2025

(54) AUXILIARY DEVICE FOR IMPLANTING ORTHOPEDIC PEDICLE SCREWS

(71) Applicant: Qingdao Shunfengda Medical Technology Workroom, Shandong (CN)

(72) Inventor: Naixi Liu, Shandong (CN)

(73) Assignee: Qingdao Shunfengda Medical Technology Workroom, Qingdao (CN)

( * ) Notice: Subject to any disclaimer, the term of this patent is extended or adjusted under 35 U.S.C. 154(b) by 466 days.

(21) Appl. No.: 17/829,198

(22) Filed: May 31, 2022

(65) Prior Publication Data

US 2022/0287780 A1    Sep. 15, 2022

(30) Foreign Application Priority Data

Jul. 8, 2021    (CN) .......................... 202110775923.4

(51) Int. Cl.
- *A61B 34/20*    (2016.01)
- *A61B 6/00*    (2024.01)
- *A61B 17/88*    (2006.01)
- *B66F 3/44*    (2006.01)
- *B66F 7/14*    (2006.01)

(52) U.S. Cl.
CPC ............ *A61B 34/20* (2016.02); *A61B 6/4405* (2013.01); *A61B 6/4435* (2013.01); *A61B 17/88* (2013.01); *B66F 3/44* (2013.01); *B66F 7/14* (2013.01)

(58) Field of Classification Search
CPC ..... A61B 34/20; A61B 6/4405; A61B 6/4435; A61B 6/4476; A61B 6/56; A61B 17/88; A61B 17/1671; A61B 17/1703; A61B 17/1757; A61B 17/92; A61B 2090/376; B66F 3/44; B66F 7/14

See application file for complete search history.

(56) References Cited

U.S. PATENT DOCUMENTS

2020/0121267 A1*    4/2020    Deutschmann ...... A61B 6/4452

* cited by examiner

*Primary Examiner* — Peter Luong
(74) *Attorney, Agent, or Firm* — Ming Jiang; MM IP SERVICES LLC

(57) ABSTRACT

An auxiliary device for implanting orthopedic pedicle screws includes a first bearing and a slip ring. The first bearing includes an outer ring and an inner ring, the slip ring is fixed with the inner ring, a brush is set between the slip ring and the outer ring, an X-ray light source and an X-ray receiver opposite to the X-ray light source are set on the inner ring, a drive mechanism is set on an external surface of the outer ring, a support device is set at left and right ends of the outer ring in a radial direction thereof; a swing device is provided at an upper portion of the support device, a workbench is provided at a lower portion of the support device, the swing device is connected with the outer ring. A skid platform unit, a lifting device and a rotating device are set on the workbench.

10 Claims, 14 Drawing Sheets ously, the first C-arm and the second C-arm are able to be independently adjusted, and no other auxiliary equipment is provided, so the device is unable to move in other directions.

AUXILIARY DEVICE FOR IMPLANTING ORTHOPEDIC PEDICLE SCREWS

CROSS REFERENCE OF RELATED APPLICATION

The present invention claims priority under 35 U.S.C. 119(a-d) to CN 202110775923.4, filed Jul. 8, 2021.

BACKGROUND OF THE PRESENT INVENTION

Field of Invention

The present invention relates to the field of orthopedic surgical auxiliary instruments, and more particularly to an auxiliary device for implanting orthopedic pedicle screws.

Description of Related Arts

During orthopedic pedicle surgery, fluoroscopy equipment is usually required to assist in determining the location of the pedicle drilling. At present, "C"-shaped arm X-ray machines and "G"-shaped arm X-ray machines are the common fluoroscopy equipment. The "C"-shaped arm X-ray machines are able to be rotated, but are unable to see through the frontal and lateral positions at the same time; the "G"-shaped arm X-ray machines are able to see through the frontal and lateral positions at the same time, but are unable to be rotated. Therefore, it is inconvenient for surgery, and it is easy to accidentally injure the dural sac and nerve root in the spinal canal, resulting in serious complications such as paralysis and cerebrospinal fluid leakage, which brings pain to patients and makes the relationship between doctors and patients tense.

Patent document CN 106175917 A discloses an auxiliary device for implanting sliding cross-fluoroscopy orthopedic pedicle screws. The auxiliary device includes a guide rod, a sliding cylinder, sleeves and a pedicle drill all of which are coaxially set, wherein an axis of the guide rod, the sliding cylinder, the sleeves and the pedicle drill coincides with a central axis of a beam limiter, a ray source and a receiving device. The B-arc is used to guide the direction of the screw implantation, and the A-arc is used to prevent the screw from being implanted too deep. Moreover, the first sleeve is able to move left and right. The second drive motor is able to drive the rack and pinion to drive the B-arc to rotate along the A-arc in both clockwise and counterclockwise directions. The third sleeve moves up and down, and the rotating motor drives the meshing gear to rotate, thereby driving the transmission shafts of the front, rear, left and right wheels to rotate. A variety of buttons are set on the controller, which is convenient to control the device to move in different directions, and the variety of buttons are used in conjunction with the display screen to facilitate the accurate implantation of the pedicle screw and the manipulation of the entire device. The device is able to move up and down through a stand column, a support arm is used to control the A-arc and B-arc to move left and right and to rotate back and forth, so it is unstable for transmission and is still prone to deviation, resulting in inaccurate positioning. In addition, the A-arc and the B-arc are unable to completely rotate a circle, causing inconvenience in post image processing.

Patent document CN 104434156 A discloses a double C-arm structure and an imaging device for biplanar X-ray imaging equipment, wherein the double C-arm structure includes a first C-arm and a second C-arm. The first C-arm is slidably mounted on the sliding and rotating seat through the first support and limit device. The second C-arm is slidably mounted on the sliding and rotating seat through the second support and limit device. The first C-arm and the second C-arm are able to independently slide from each other, and do not affect each other while working. Moreover, compared with existing double C-arm structures, the double C-arm structure disclosed by CN 104434156 A is simple in structure and convenient in usage. During the operation, the first C-arm and the second C-arm are able to be adjusted independently, which reduces the surgical risk and the operation time compared with the prior art. However, in the double C-arm structure disclosed by CN 104434156 A, the first C-arm and the second C-arm are able to be independently adjusted, and no other auxiliary equipment is provided, so the device is unable to move in other directions.

SUMMARY OF THE PRESENT INVENTION

An object of the present invention is to overcome the above technical defects, and to propose an auxiliary device for implanting orthopedic pedicle screws. The auxiliary device is stable in operation, high in positioning accuracy, and capable of adjusting and positioning in multiple directions.

To achieve the above object, the present invention adopts technical solutions as follows.

An auxiliary device for implanting orthopedic pedicle screws comprises a first bearing and a slip ring, wherein:
the first bearing comprises an outer ring and an inner ring both of which is able to slide relatively to each other, the slip ring is fixed with the inner ring of the first bearing, a brush is set between the slip ring and the outer ring, an X-ray light source and an X-ray receiver which is opposite to the X-ray light source are set on the inner ring, a drive mechanism is set on an external surface of the outer ring for driving the inner ring to rotate, a support device is set at left and right ends of the outer ring in a radial direction thereof;
a swing device is provided at an upper portion of the support device, a workbench is provided at a lower portion of the support device, the swing device is connected with the outer ring, all of a skid platform unit, a lifting device and a rotating device are set on the workbench, the skid platform unit is able to move back and forth, left and right, the lifting device is able to move up and down, the rotating device is able to rotate, the first bearing is able to rotate axially and to swing back and forth under an action of the swing device.

Preferably, the X-ray light source comprises a beam limiter, wherein a bulb tube and an X-ray stopper are provided within the beam limiter, the X-ray stopper is located at an inner side or an outer side of the bulb tube, the X-ray stopper has a through hole in a center thereof, the through hole is used to allow X-rays emitted by the bulb tube to pass through;
the through hole provided in the center of the X-ray stopper is rectangular, isosceles trapezoidal or hourglass-shaped;
the X-ray receiver is used to receive the X-rays and transmit the X-rays to other elements.

Preferably, the X-ray light source and the X-ray receiver are connected with the inner ring through a guiding device; the guiding device comprises a clamping device, a first transverse connecting rod, a longitudinal connecting rod, a second transverse connecting rod and a sleeve, wherein the clamping device is circular and coaxial with the X-rays, one end of the first transverse connecting rod is connected with the clamping device through a chuck, another end of the first transverse connecting rod is connected with an upper end of the longitudinal connecting rod, one end of the second transverse connecting rod is connected with the sleeve, and another end of the second transverse connecting rod is connected with a lower end of the longitudinal connecting rod;

the chuck is able to slide along a circumference of the clamping device, an extension line of the first transverse connecting rod passes through a center of the clamping device, the longitudinal connecting rod is a lead screw and is able to axially slide, the clamping device and the sleeve are coaxial with the X-rays; an axis of the first transverse connecting rod, an axis of the longitudinal connecting rod and an axis of the second transverse connecting rod are provided in a same plane.

Preferably, a longitudinal section of the inner ring of the first bearing is convex, the outer ring is provided at two shoulder portions of the inner ring, the slip ring is fixed with the inner ring through a bolt, the drive mechanism which is set on the external surface of the outer ring comprises a drive motor and a timing belt, the drive motor is connected with the outer ring through a motor connection plate, a driving gear is set on the drive motor, a driven gear is set on an external surface of the inner ring, and the timing belt is provided between the driving gear and the driven gear.

Preferably, the slip ring is fixed with the inner ring through a bolt, the drive mechanism which is set on the external surface of the outer ring comprises a drive motor, a driving gear is set on the drive motor, a driven gear is set on an external surface of the inner ring, the driving gear is engaged with the driven gear for driving the driven gear to rotate.

Preferably, the swing device comprises a swing motor, a swing reducer, a swing shaft and a leather belt, wherein an output shaft of the swing motor is connected with an input shaft of the swing reducer through gear transmission, a driving pulley is provided on an output shaft of the swing reducer, the swing shaft is horizontally set on an upper end of the support device through a swing bearing, a driven pulley is provided at an outer end of the swing shaft, an inner end of the swing shaft is connected with the outer ring through a connection block, the leather belt is provided between the driving pulley and the driven pulley.

Preferably, the swing device comprises a swing motor, a swing reducer, a swing shaft, a driving swing gear and a driven swing gear, wherein an output shaft of the swing motor is connected with an input shaft of the swing reducer through gear transmission, the driving swing gear is provided on an output shaft of the swing reducer, the swing shaft is horizontally set on an upper end of the support device through a swing bearing, the driven swing gear is provided at an outer end of the swing shaft, an inner end of the swing shaft is connected with the outer ring through a connection block, the driving swing gear is engaged with the driven swing gear for driving the driven swing gear to rotate.

Preferably, the rotating device comprises a tray, wherein the tray has a tray hole in a center thereof, a rotating motor and a rotating reducer are located under the tray, a rotating disk is located on the tray, the rotating reducer is connected with the rotating motor, an output shaft of the rotating reducer passes through the tray hole and is connected with the rotating disk, so that the rotating motor is able to drive the rotating disk to rotate;

the support device has a U-shaped structure, an upper portion of the rotating disk is connected with a lower portion of a transverse plate of the U-shaped structure, two rotating sliders are respectively provided at left and right sides of the transverse plate, an arc-shaped slide rail is provided on an upper surface of the tray, the rotating sliders are locked on the arc-shaped slide rail, so that with a rotation of the rotating disk, the transverse plate is driven to rotate, so as to drive the rotating sliders to slide along the arc-shaped slide rail.

Preferably, the lifting device comprises a lifting screw and a lifting motor, wherein an upper end of the lifting screw is connected with a lower surface of the tray, a lower end of the lifting screw is provided on the lifting motor, the lifting motor is provided within the skid platform unit, so that the lifting motor rotates to drive the lifting screw to move up and down, so as to further drive the tray to move up and down.

Preferably, the skid platform unit comprises an outside skid platform, a middle skid platform and an inside skid platform, wherein the middle skid platform is sleeved within the outside skid platform and is able to move left and right along the outside skid platform, the inside skid platform is sleeved within the middle skid platform and is able to move back and forth along the middle skid platform, the lifting screw and the lifting motor are provided within the inside skid platform;

a first slide rail, a first lead screw, a first lead screw motor and a first bracket are provided on the outside skid platform; the first lead screw motor is provided on the first bracket, one end of the first lead screw is connected with an output shaft of the first lead screw motor, and another end of the first lead screw passes through the first bracket and is provided on the middle skid platform;

a first slider fitted with the first slide rail is provided at an outer side of the middle skid platform; a second slide rail, a second lead screw, a second lead screw motor and a second bracket are provided at an inner side of the middle skid platform; the second lead screw motor is provided on the second bracket, one end of the second lead screw is connected with an output shaft of the second lead screw motor, and another end of the second lead screw passes through the second bracket and is provided on the inside skid platform;

a second slider fitted with the second slide rail is provided at an outer side of the inside skid platform, an inner side of the inside skid platform has a vertical round passage as a lifting slideway, and the lifting screw is sleeved within the lifting slideway.

The present invention has some beneficial effects as follows. The inside skid platform of the skid platform unit realizes the adjustment of the front and rear directions of the workbench, the middle skid platform realizes the adjustment of the left and right directions of the workbench, and the lifting device realizes the adjustment of the up and down directions of the workbench. The rotating device realizes that the support device rotates around the vertical centerline thereof, thereby driving the combination of the first bearing and the slip ring to rotate around the vertical centerline thereof. The swing motor rotates for driving the combination of the first bearing and the slip ring to rotate around the horizontal center line thereof, so that the combination of the first bearing and the slip ring swings in the front and rear directions. The outer ring and the inner ring of the first bearing are able to move relative to each other, and in combination with the X-ray light source and the X-ray receiver, according to the rays emitted by the X-ray light source, the position where the pedicle screw needs to be implanted is able to be found under fluoroscopy. A guide rod, a sliding cylinder and a sleeve of the guiding device have the same axis as a pedicle drill, and the axis coincides with a central axis of the X-ray stopper, the bulb tube and an image intensifier to ensure that when the pedicle drill is drilling, the guide wire is precisely aligned with the drilling position to avoid deflection. The through hole provided in the center of the X-ray stopper is rectangular, isosceles trapezoidal or hourglass-shaped for blocking the rays scattered by the anode and leaving the precise rays, so as to assist the positioning of the pedicle drilling.

Figure 1:
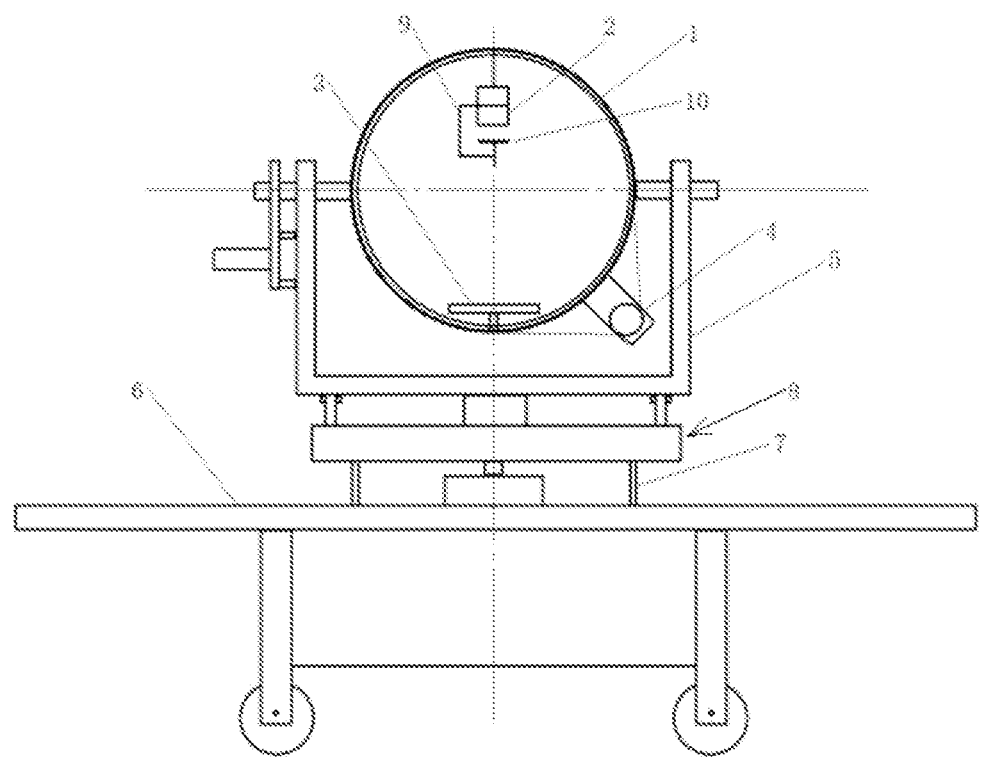
FIG. 1 is a structural schematic diagram of an auxiliary device for implanting orthopedic pedicle screws provided by the present invention.
Figure 2:
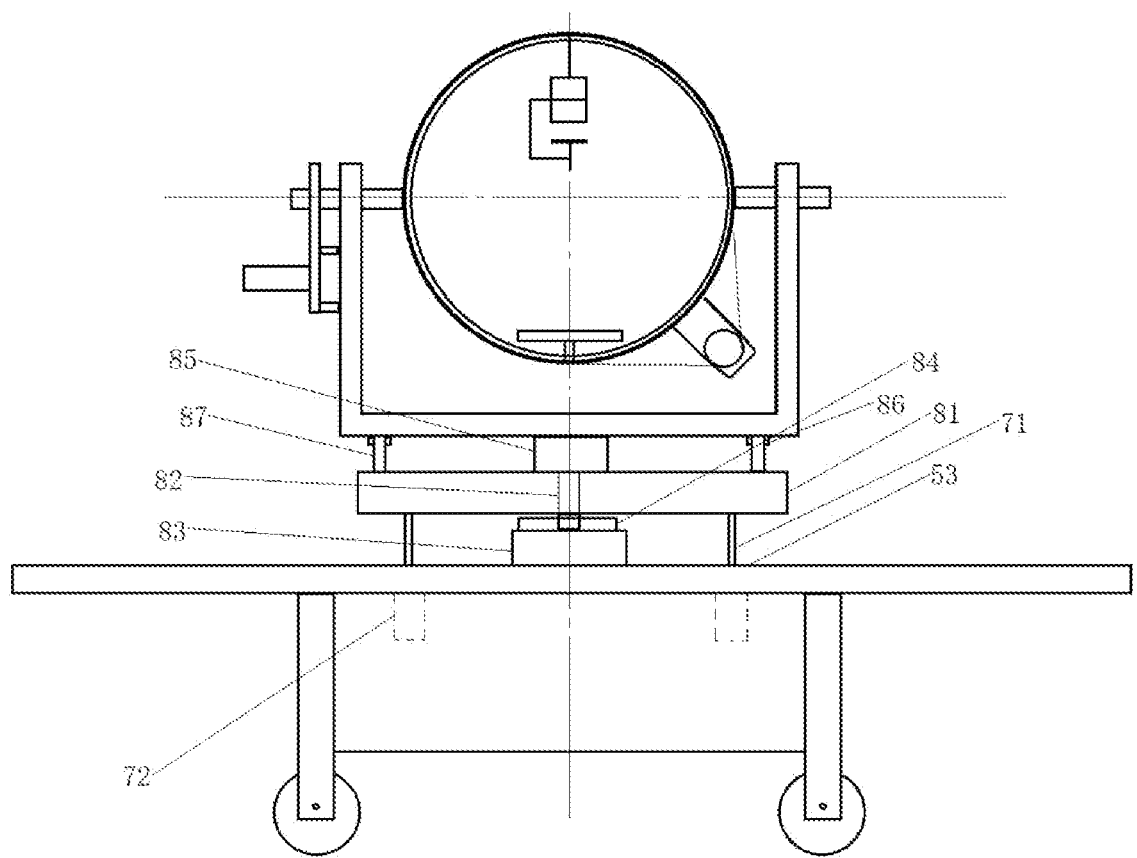
FIG. 2 is a structural schematic diagram of a lifting device and a rotating device of the auxiliary device.

In the drawings, 1: first bearing; 100: slip ring; 11: outer ring; 12: inner ring; 13: brush; 14: bolt; 2: X-ray light source; 3: X-ray receiver; 4: drive mechanism; 5: support device; 6: skid platform unit; 7: lifting device; 8: rotating device; 9: guiding device; 10: pedicle drill; 21: beam limiter; 211: bulb tube; 212: X-ray stopper; 213: through hole; 41: drive motor; 42: timing belt; 43: motor connection plate; 44: driving gear; 45: driven gear; 52: swing device; 53: workbench; 521: swing motor; 522: swing reducer; 523: swing shaft; 524: leather belt; 525: driving pulley; 526: swing bearing; 527: driven pulley; 528: connection block; 529: driving swing gear; 530: driven swing gear; 61: outside skid platform; 62: middle skid platform; 63: inside skid platform; 64: first slide rail; 65: first lead screw; 66: first lead screw motor; 67: first bracket; 68: first slider; 69: second slide rail; 610: second lead screw; 611: second lead screw motor; 612: second bracket; 613: second slider; 614: vertical round passage; 71: lifting screw; 72: lifting motor; 81: tray; 82: tray hole; 83: rotating motor; 84: rotating reducer; 85: rotating disk; 86: rotating slider; 87: arc-shaped slide rail; 91: clamping device; 92: first transverse connecting rod; 93: longitudinal connecting rod; 94: second transverse connecting rod; 95: sleeve; 96: chuck; 97: mounting bracket.

DETAILED DESCRIPTION OF THE PREFERRED EMBODIMENT

The present invention is further explained with accompanying drawings and embodiments as follows in detail.

First Embodiment

Referring to FIGS. 1-2, 4-5, 9-15 and 17-21, an auxiliary device for implanting orthopedic pedicle screws is illustrated. The auxiliary device comprises a first bearing 1 and a slip ring 100, wherein the first bearing 1 comprises an outer ring 11 and an inner ring 12 both of which is able to slide relatively to each other, the slip ring 100 is fixed with the inner ring 12 of the first bearing 1. A brush 13 is set between the slip ring 100 and the outer ring 11. An X-ray light source 2 and an X-ray receiver 3 which is opposite to the X-ray light source 2 are set on the inner ring 12. A drive mechanism 4 is set on an external surface of the outer ring 11 for driving the inner ring 12 to rotate. A support device 5 is set at left and right ends of the outer ring 11 in a radial direction thereof.

A swing device 52 is provided at an upper portion of the support device 5, a workbench 53 is provided at a lower portion of the support device 5, and the swing device 52 is connected with the outer ring 11. A skid platform unit 6, a lifting device 7 and a rotating device 8 are set on the workbench 53. The skid platform unit 6 is able to move back and forth, left and right. The lifting device 7 is able to move up and down. The rotating device 8 is able to rotate. The first bearing 1 is able to rotate axially, and swing back and forth under an action of the swing device 52.

The X-ray light source 2 comprises a beam limiter 21, wherein a bulb tube 211 and an X-ray stopper 212 are provided within the beam limiter 21, the X-ray stopper 212 is located at an inner side or an outer side of the bulb tube 211, the X-ray stopper 212 has a through hole 213 in a center thereof, the through hole 213 is used to allow X-rays emitted by the bulb tube 211 to pass through.

The through hole 213 provided in the center of the X-ray stopper 212 is rectangular, isosceles trapezoidal or hourglass-shaped.

The X-ray receiver 3 is used to receive the X-rays and transmit the X-rays to other elements.

The X-ray light source 2 and the X-ray receiver 3 are connected with the inner ring 12 through a guiding device 9.

The guiding device 9 comprises a clamping device 91, a first transverse connecting rod 92, a longitudinal connecting rod 93, a second transverse connecting rod 94 and a sleeve 95, wherein the clamping device 91 is circular and coaxial with the X-rays, one end of the first transverse connecting rod 92 is connected with the clamping device 91 through a chuck 96, another end of the first transverse connecting rod 92 is connected with an upper end of the longitudinal connecting rod 93, one end of the second transverse connecting rod 94 is connected with the sleeve 95, and another end of the second transverse connecting rod 94 is connected with a lower end of the longitudinal connecting rod 93.

The chuck 96 is able to slide along a circumference of the clamping device 91, an extension line of the first transverse connecting rod 92 passes through a center of the clamping device 91, the longitudinal connecting rod 93 is a lead screw and is able to axially slide. The clamping device 91 and the sleeve 95 are coaxial with the X-rays. An axis of the first transverse connecting rod 92, an axis of the longitudinal connecting rod 93 and an axis of the second transverse connecting rod 94 are provided in a same plane.

The clamping device is able to be set at an outer edge of the beam limiter or the X-ray receiver, that is, the clamping device is able to be independently set at the outer edge of the beam limiter or the X-ray receiver, or two clamping devices are able to be set at the outer edge of the beam limiter and the X-ray receiver.

A longitudinal section of the inner ring 12 is convex, the outer ring 11 is provided at two shoulder portions of the inner ring 12. The slip ring 100 is fixed with the inner ring 12 through a bolt 14. The drive mechanism 4, which is set on the external surface of the outer ring 11, comprises a drive motor 41 and a timing belt 42, wherein the drive motor 41 is connected with the outer ring 11 through a motor connection plate 43, a driving gear 44 is set on the drive motor 41, a driven gear 45 is set on an external surface of the inner ring 12, and the timing belt 42 is provided between the driving gear 44 and the driven gear 45.

The swing device 52 comprises a swing motor 521, a swing reducer 522, a swing shaft 523 and a leather belt 524, wherein an output shaft of the swing motor 521 is connected with an input shaft of the swing reducer 522 through gear transmission, a driving pulley 525 is provided on an output shaft of the swing reducer 522, the swing shaft 523 is horizontally set on an upper end of the support device 5 through a swing bearing 526, a driven pulley 527 is provided at an outer end of the swing shaft 523, an inner end of the swing shaft 523 is connected with the outer ring 11 through a connection block 528, the leather belt 524 is provided between the driving pulley 525 and the driven pulley 527.

The rotating device 8 comprises a tray 81, wherein the tray 81 has a tray hole 82 in a center thereof, a rotating motor 83 and a rotating reducer 84 are located under the tray 81, a rotating disk 85 is located on the tray 81, the rotating reducer 84 is connected with the rotating motor 83, an output shaft of the rotating reducer 84 passes through the tray hole 82 and is connected with the rotating disk 85, so that the rotating motor 83 is able to drive the rotating disk 85 to rotate.

The support device 5 has a U-shaped structure. An upper portion of the rotating disk 85 is connected with a lower portion of a transverse plate of the U-shaped structure. Two rotating sliders 86 are provided at left and right sides of the transverse plate, respectively. An arc-shaped slide rail 87 is provided on an upper surface of the tray 81. The rotating sliders 86 are locked on the arc-shaped slide rail 87. With the rotation of the rotating disk 85, the transverse plate is driven to rotate, so as to drive the rotating sliders 86 to slide along the arc-shaped slide rail 87.

The lifting device 7 comprises two lifting screws 71 and two lifting motors 72, wherein two upper ends of the lifting screws 71 are connected with a lower surface of the tray 81, two lower ends of the lifting screws 71 are respectively provided on the lifting motors 72, the lifting motors 72 are provided within the skid platform unit 6. The lifting motors 72 respectively rotate to drive the lifting screws 71 to move up and down, so as to further drive the tray 81 to move up and down.

The skid platform unit 6 comprises an outside skid platform 61, a middle skid platform 62 and an inside skid platform 63, wherein the middle skid platform 62 is sleeved within the outside skid platform 61 and is able to move left and right along the outside skid platform 61, the inside skid platform 63 is sleeved within the middle skid platform 62 and is able to move back and forth along the middle skid platform 62, the lifting screws 71 and the lifting motors 72 are provided within the inside skid platform 63.

A first slide rail 64, a first lead screw 65, a first lead screw motor 66 and a first bracket 67 are provided on the outside skid platform 61. The first lead screw motor 66 is provided on the first bracket 67. One end of the first lead screw 65 is connected with an output shaft of the first lead screw motor 66, and another end of the first lead screw 65 passes through the first bracket 67 and is provided on the middle skid platform 62.

A first slider 68 fitted with the first slide rail 64 is provided at an outer side of the middle skid platform 62. A second slide rail 69, a second lead screw 610, a second lead screw motor 611 and a second bracket 612 are provided at an inner side of the middle skid platform 62. The second lead screw motor 611 is provided on the second bracket 612. One end of the second lead screw 610 is connected with an output shaft of the second lead screw motor 611, and another end of the second lead screw 610 passes through the second bracket 612 and is provided on the inside skid platform 63.

A second slider 63 fitted with the second slide rail 69 is provided at an outer side of the inside skid platform 63, an inner side of the inside skid platform 63 has a vertical round passage 614 as a lifting slideway, and the lifting screws 71 are sleeved within the lifting slideway.

The working principle and the working process of the present invention are described as follows.

The present invention discloses a six-axis system which includes three linear motions and three rotational motions. The six-axis system and the X-rays form the whole system for finding an axis of a target object in an area, that is, the axis of the pedicle. After the axis is found, combined with a guide sleeve system, a screw is implanted into the target object, namely, the pedicle.

The relationship between motion and positioning is as follows.

(1) A posterior anterior long axis of the spine is observed by moving left and right.
(2) Upper and lower edges of the target vertebral body are observed by moving back and forth.
(3) The base is rotated to see that upper and lower edges of the vertebral body are flush in the lateral view.
(4) The intersection of pedicles on both sides is estimated by lifting adjustment.
(5) Upper and lower edges of the pedicle of the posterior anterior vertebral body are observed by swinging and rotating.

(6) The axis of the pedicle is observed by rotate the inner ring of the first bearing.

Specifically, in order to facilitate pushing the workbench 53, four wheels are provided at four corners and a bottom of the outside skid platform 63, so that the workbench 53 is easy to be pushed to the operating room through the wheels.

The first bearing 1 comprise the outer ring 11 and the inner ring 12, the X-ray light source 2 and the X-ray receiver 3 are provided on the inner ring 12. The workbench 53 is pushed along the operating bed, the inner ring 12 moves along the operating bed till the workbench 53 moves to the patient's spine where the pedicle screw needs to be implanted.

Figure 18:
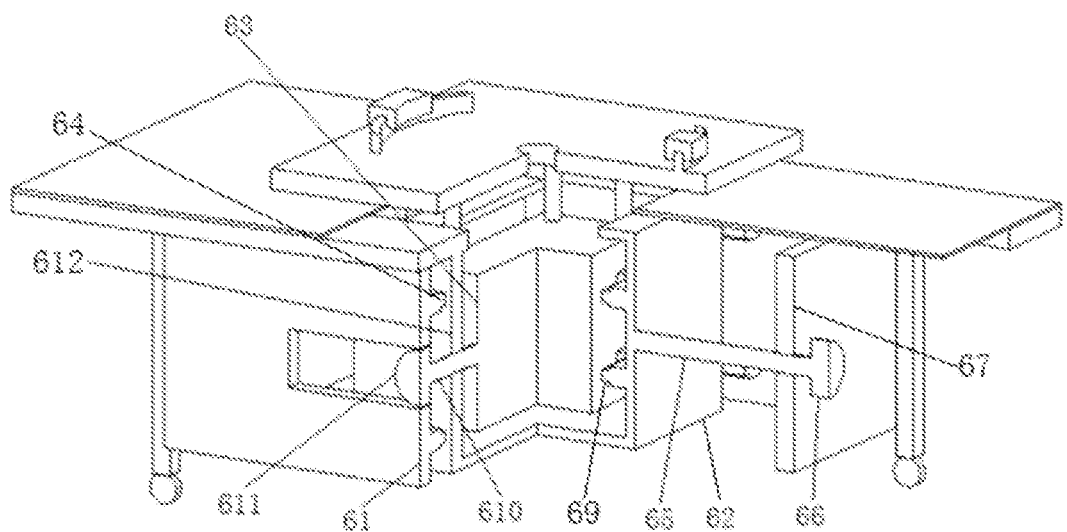
FIG. 18 is a sectional view of the skid platform unit.
Figure 19:
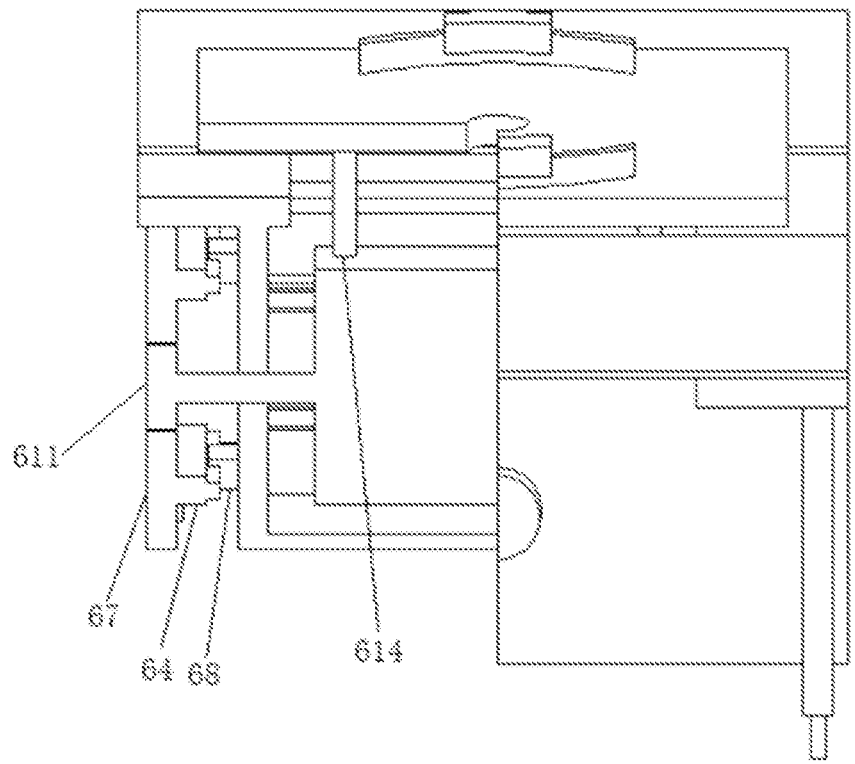
FIG. 19 is a schematic diagram of the connection between the first slide rail and the first slider of the auxiliary device.
Figure 20:
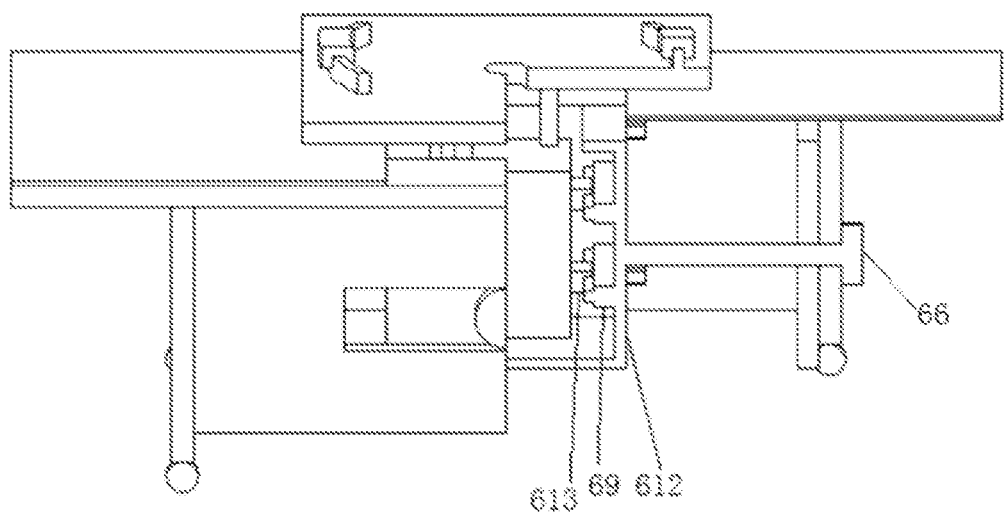
FIG. 20 is a schematic diagram of the connection between the second slide rail and the second slider of the auxiliary device.
Figure 21:
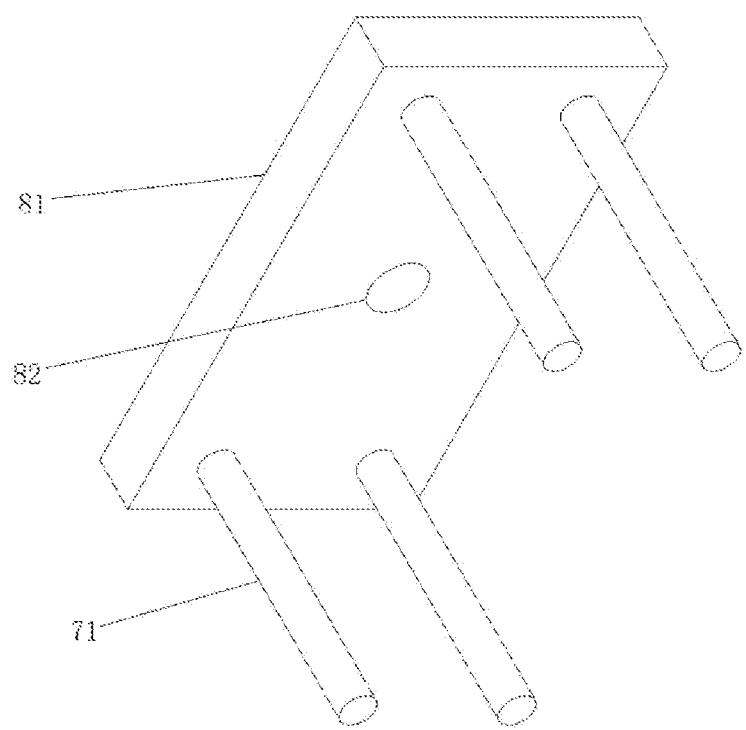
FIG. 21 is a structural schematic diagram of a tray and a lifting screw of the auxiliary device.

After the first bearing 1 and the slip ring 100 are wholly moved to a proper position, the second lead screw motor 611 drives the second lead screw 610 to rotate, so as to drive the second slider 613 on the inside skid platform 63 to move along the second slide rail 69, thus further driving the lifting lead screws 71 and the lifting motors 72 to move back and forth to realize the adjustment of the front and rear directions of the workbench 53, as shown in FIGS. 18-20.

The first lead screw motor 66 drives the first lead screw 65 to rotate, so as to drive the first slider 68 on the middle skid platform 62 to move along the first slide rail 64, thus further driving the inside skid platform 63, the lifting lead screws 71 and the lifting motors 72 to move left and right to realize the adjustment of the left and right directions of the workbench 53, as shown in FIGS. 18-20.

Figure 17:
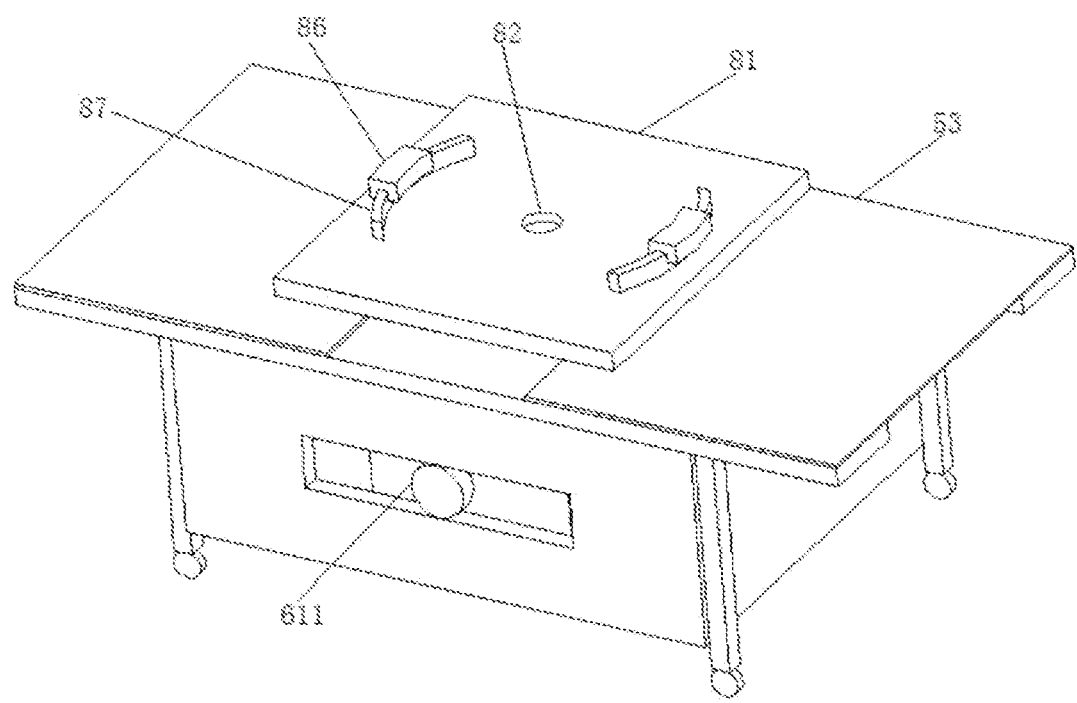
FIG. 17 is a structural schematic view of a skid platform unit of the auxiliary device.

The lifting motors 72 are started to drive the lifting lead screws 71 to rotate, so as to further drive the tray 81 to move up and down, thereby achieving the adjustment of the up and down directions of the workbench 53, as shown in FIG. 17.

After completing the adjustment of the front and rear, left and right, and up and down directions of the workbench, the auxiliary device provided by the present invention is rotated and adjusted. The rotating motor 83 drives the rotating disk 85 to rotate. With the rotation of the rotating disk 85, the transverse plate of the U-shaped structure of the support device 5 is driven to rotate, so as to drive the rotating sliders 86 to slide along the arc-shaped slide rail 87, thereby the support device 5 rotates around a vertical centerline thereby, for further driving the first bearing 1 and the slip ring 100 as a whole to rotate around a vertical centerline of the first bearing 1 and the slip ring 100.

The swing motor 521 rotates to drive the driving pulley 525, the leather belt 524 and the driven pulley 527 to rotate, so as to drive the first bearing 1 and the slip ring 100 to rotate around a horizontal centerline thereof, thereby achieving the swing of the first bearing 1 and the slip ring 100 in the front and rear directions.

The drive mechanism 4 is provided on the external surface of the outer ring 11, the driving gear 44 is provided on the driving motor 41, the driven gear 45 is provided on the inner ring 12, and the timing belt 42 is provided between the driving gear 44 and the driven gear 45. The driving motor 41 drives the inner ring 12 to rotate relatively to the outer ring 11. With the rotation of the inner ring 12, based on the X-rays emitted by the X-ray light source 2, the location where the pedicle screw needs to be implanted under fluoroscopy is found.

The X-ray light source 2 comprises the beam limiter 21, the bulb tube 211 and the X-ray stopper 212 are provided within the beam limiter, the X-ray stopper 212 has the through hole 213 in the center thereof, the through hole 213 is used to allow the X-rays emitted by the bulb tube 211 to pass through. The through hole 213 provided in the center of the X-ray stopper 212 is rectangular, isosceles trapezoidal or hourglass-shaped. In this way, the X-rays emitted by the bulb tube 211 is able to form a precise projection and assist the positioning of the pedicle drilling.

The X-ray receiver 3 is equipped with a wireless image transmission system. The wireless image transmission system transmits the signal transmitted by the X-ray receiver 3 to the wireless signal receiver and transmits to a computer in a wireless manner, so as to realize the reading of the pedicle drilling positioning picture and the real-time drilling working picture on the display, and improve the pedicle drilling accuracy and the pedicle screw implantation accuracy.

Second Embodiment

Figure 3:
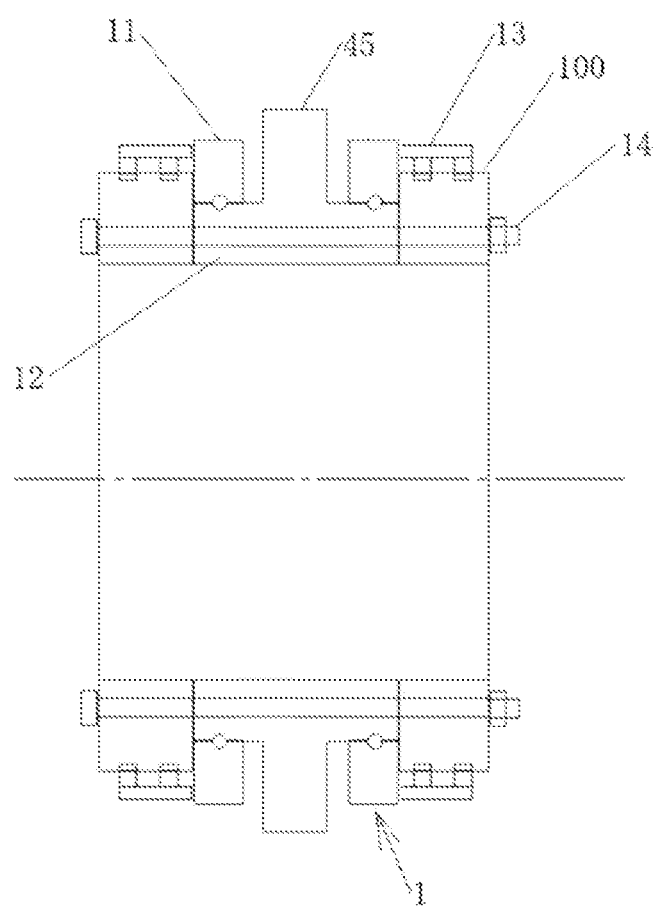
FIG. 3 is a schematic diagram of the first connection method among a slip ring, a first bearing and a driven gear of the auxiliary device.
Figure 4:
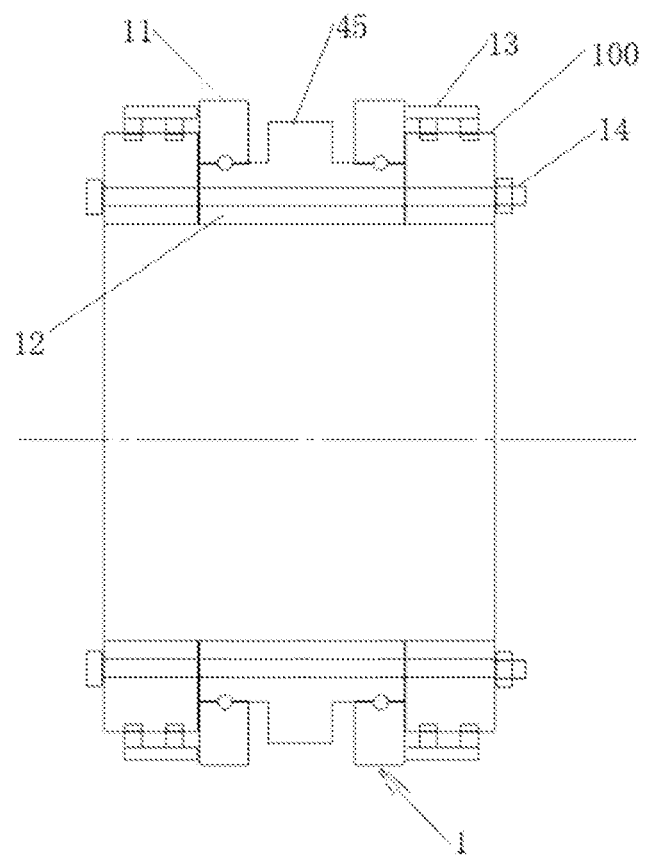
FIG. 4 is a schematic diagram of the second connection method among the slip ring, the bearing and the driven gear of the auxiliary device.
Figure 5:
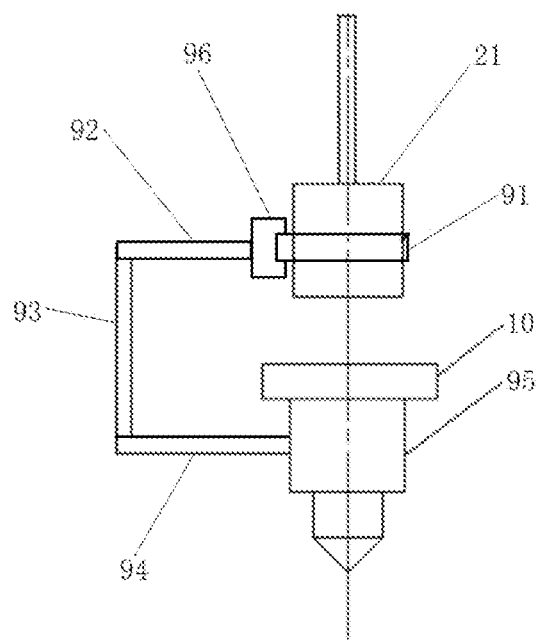
FIG. 5 is a schematic diagram of the connection between a guiding device and an X-ray light source of the auxiliary device.
Figure 16:
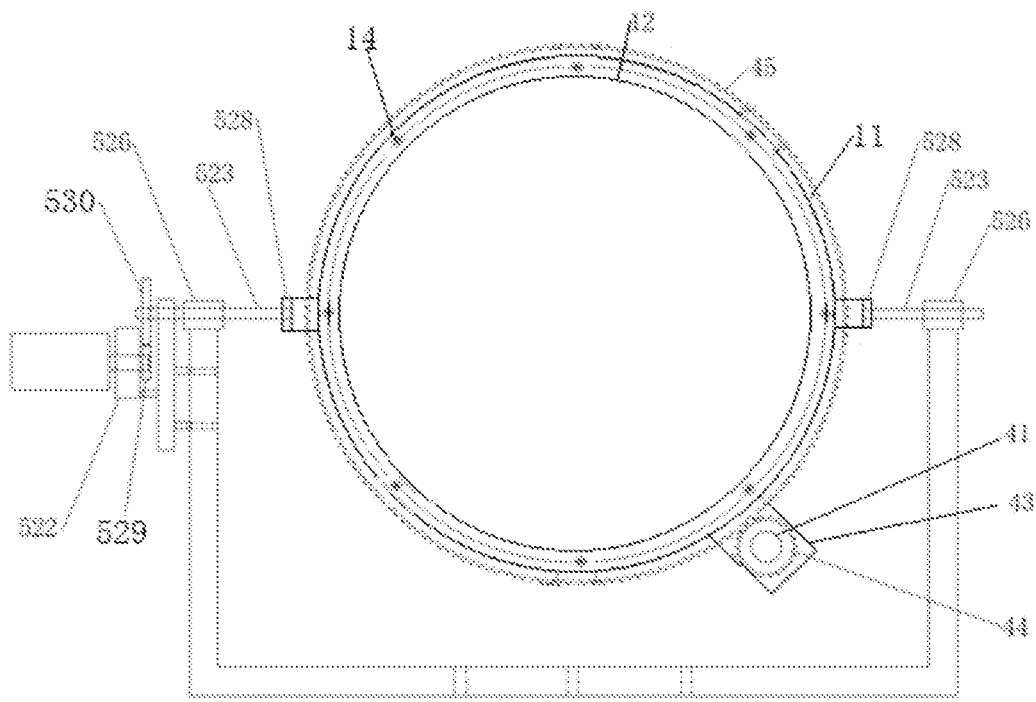
FIG. 16 is another structural schematic diagram of the combination of the first bearing and the slip ring and the swing device.

Referring to FIGS. 3 and 16, the drive mechanism 4, which is provided at the external surface of the outer ring 11 of the first bearing 1, comprises a drive motor 41, wherein the driving gear 44 is provided on the drive motor 41, the driven gear 45 is provided on the inner ring 12, the driving gear 44 is engaged with the driven gear 45 for driving the driven gear 45 to rotate.

The swing device 52 comprises a swing motor 521, a swing reducer 522, a swing shaft 523, a driving swing gear 529 and a driven swing gear 530, wherein an output shaft of the swing motor 521 is connected with an input shaft of the swing reducer 522 through gear transmission, the driving swing gear 529 is provided on an output shaft of the swing reducer 522, the swing shaft 523 is horizontally set on an upper end of the support device 5 through a swing bearing 526, the driven swing gear 530 is provided at an outer end of the swing shaft 523, an inner end of the swing shaft 523 is connected with the outer ring 11 through a connection block 528, the driving swing gear 529 is engaged with the driven swing gear 530 for driving the driven swing gear 530 to rotate.

Figure 6:
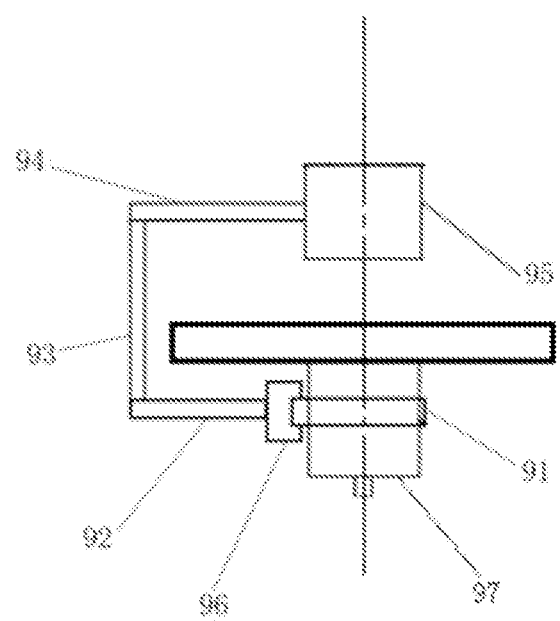
FIG. 6 is a schematic diagram of the connection between the guiding device and an X-ray receiver of the auxiliary device.
Figure 7:
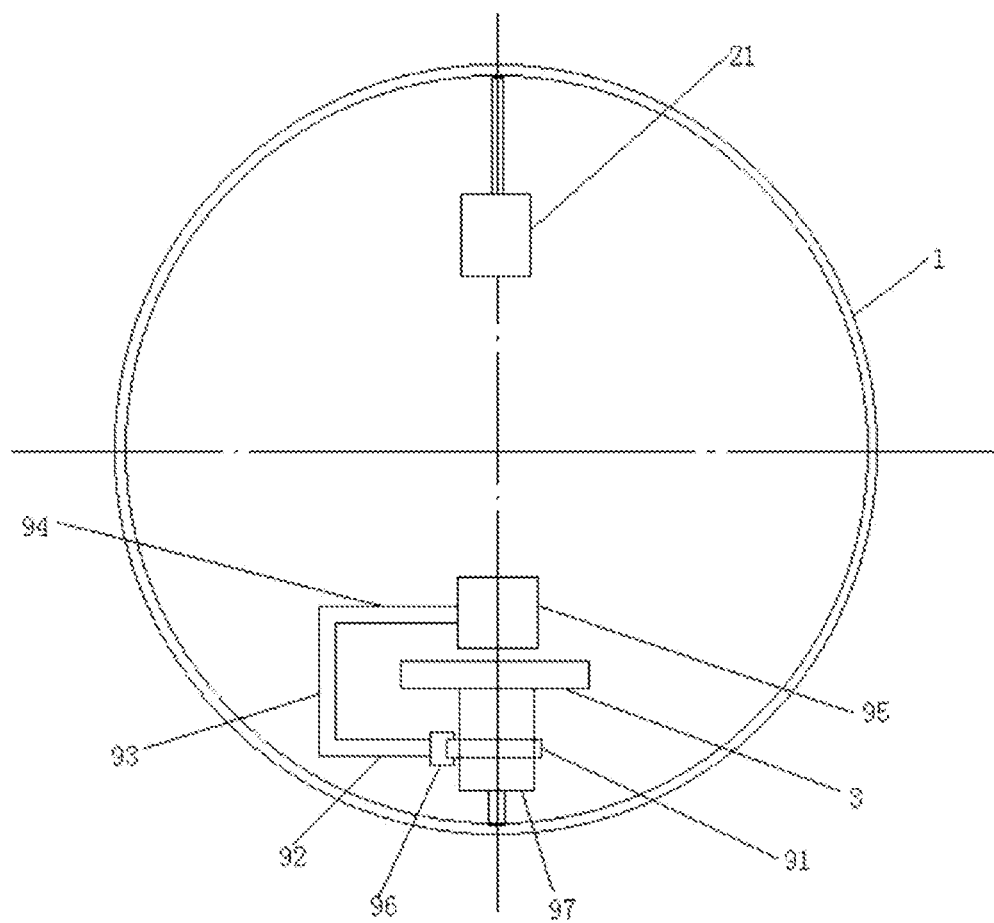
FIG. 7 is a schematic diagram of the connection between the X-ray receiver and a clamping device of the auxiliary device.
Figure 8:
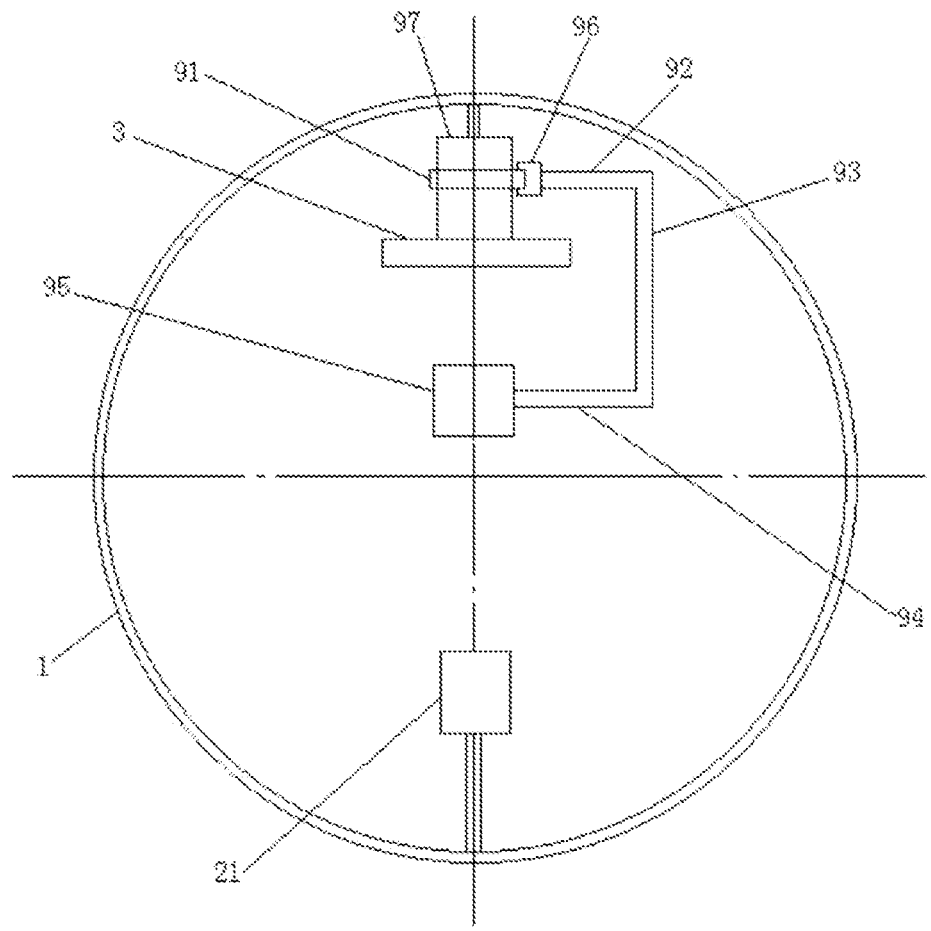
FIG. 8 is a schematic diagram of the working state when the clamping device is connected to the X-ray receiver.
Figure 9:
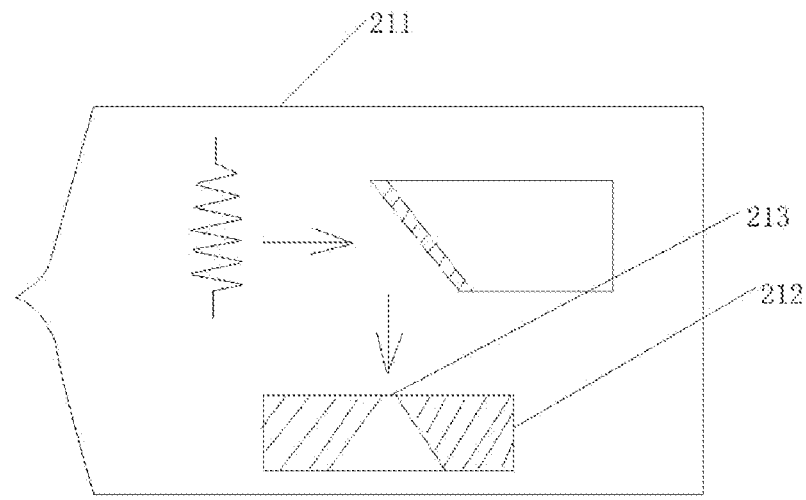
FIG. 9 is a schematic diagram of the first positional relationship between a bulb tube and an X-ray stopper of the auxiliary device.
Figure 10:
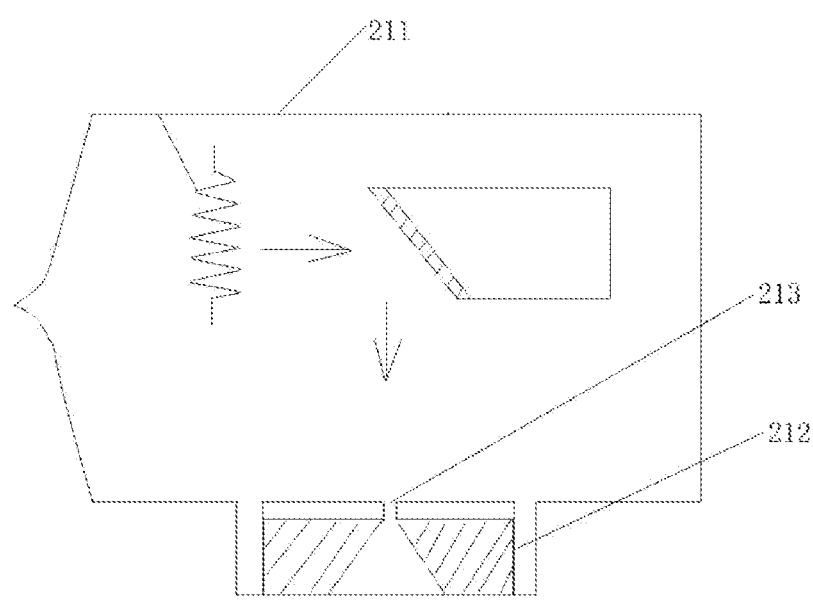
FIG. 10 is a schematic diagram of the second positional relationship between the bulb tube and the X-ray stopper.
Figure 11:
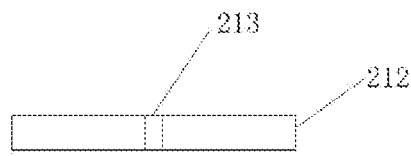
FIG. 11 is a cross-sectional view of a rectangular through hole of the X-ray stopper.
Figure 12:
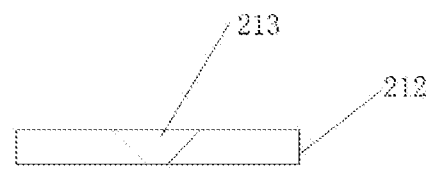
FIG. 12 is a cross-sectional view of an isosceles trapezoidal through hole of the X-ray stopper.
Figure 13:
FIG. 13 is a cross-sectional view of a hourglass-shaped through hole of the X-ray stopper.
Figure 14:
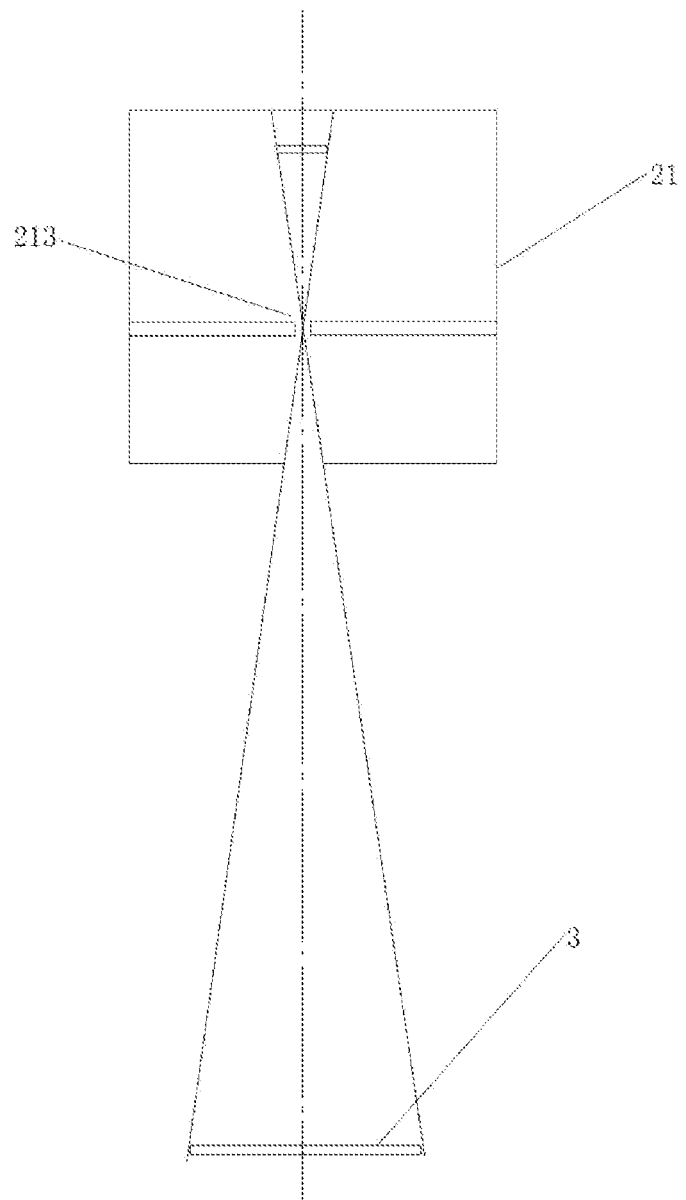
FIG. 14 is a schematic diagram of the working principle of the X-ray light source and the X-ray receiver.
Figure 15:
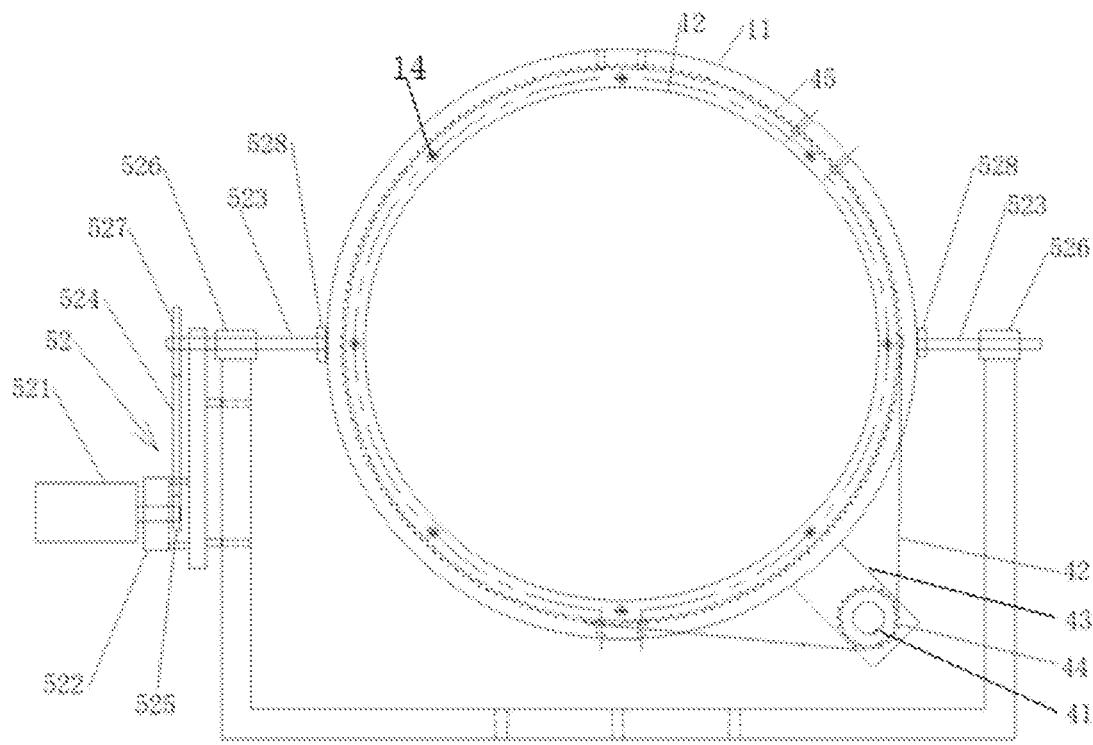
FIG. 15 is a structural schematic diagram of the combination of the first bearing and the slip ring and a swing device.

As shown in FIGS. 6 to 8, a guiding device 9 is provided on the X-ray receiver 3 for guiding screw implantation. The guiding device 9 comprises a clamping device 91, a first transverse connecting rod 92, a longitudinal connecting rod 93, a second transverse connecting rod 94 and a sleeve 95, wherein the clamping device 91 is circular and coaxial with the X-rays, one end of the first transverse connecting rod 92 is connected with the clamping device 91 through a chuck 96, another end of the first transverse connecting rod 92 is connected with an upper end of the longitudinal connecting rod 93, one end of the second transverse connecting rod 94 is connected with the sleeve 95, and another end of the second transverse connecting rod 94 is connected with a lower end of the longitudinal connecting rod 93.

The chuck 96 is able to slide along a circumference of the clamping device 91, an extension line of the first transverse connecting rod 92 passes through a center of the clamping device 91, the longitudinal connecting rod 93 is a lead screw and is able to axially slide. The clamping device 91 and the sleeve 95 are coaxial with the X-rays. An axis of the first transverse connecting rod 92, an axis of the longitudinal connecting rod 93 and an axis of the second transverse connecting rod 94 are provided in a same plane.

The clamping device 91 is able to be set at an outer edge of the X-ray light source 2 or the X-ray receiver 3, that is, the clamping device is able to be independently set at the outer edge of the beam limiter 21 of the X-ray light source 2 or the outer edge of a mounting bracket 97 of the X-ray receiver 3.

While using, the longitudinal connecting rod 93 is extended, and the pedicle drill 10 is put into the sleeve 95 to drill the pedicle.

What is claimed is:

1. An auxiliary device for implanting orthopedic pedicle screws comprises a first bearing and a slip ring, wherein:

the first bearing comprises an outer ring and an inner ring both of which is able to slide relatively to each other, the slip ring is fixed with the inner ring of the first bearing, a brush is set between the slip ring and the outer ring, an X-ray light source and an X-ray receiver which is opposite to the X-ray light source are set on the inner ring, a drive mechanism is set on an external surface of the outer ring for driving the inner ring to rotate, a support device is set at left and right ends of the outer ring in a radial direction thereof;

a swing device is provided at an upper portion of the support device, a workbench is provided at a lower portion of the support device, the swing device is connected with the outer ring, all of a skid platform unit, a lifting device and a rotating device are set on the workbench, the skid platform unit is able to move back and forth, left and right, the lifting device is able to move up and down, the rotating device is able to rotate, the first bearing is able to rotate axially and to swing back and forth under an action of the swing device.

2. The auxiliary device according to claim 1, wherein the X-ray light source comprises a beam limiter, wherein a bulb tube and an X-ray stopper are provided within the beam limiter, the X-ray stopper is located at an inner side or an outer side of the bulb tube, the X-ray stopper has a through hole in a center thereof, the through hole is used to allow X-rays emitted by the bulb tube to pass through;

the through hole provided in the center of the X-ray stopper is rectangular, isosceles trapezoidal or hourglass-shaped;

the X-ray receiver is used to receive the X-rays and transmit the X-rays to other elements.

3. The auxiliary device according to claim 1, wherein the X-ray light source and the X-ray receiver are connected with the inner ring through a guiding device; the guiding device comprises a clamping device, a first transverse connecting rod, a longitudinal connecting rod, a second transverse connecting rod and a sleeve, wherein the clamping device is circular and coaxial with the X-rays, one end of the first transverse connecting rod is connected with the clamping device through a chuck, another end of the first transverse connecting rod is connected with an upper end of the longitudinal connecting rod, one end of the second transverse connecting rod is connected with the sleeve, and another end of the second transverse connecting rod is connected with a lower end of the longitudinal connecting rod;

the chuck is able to slide along a circumference of the clamping device, an extension line of the first transverse connecting rod passes through a center of the clamping device, the longitudinal connecting rod is a lead screw and is able to axially slide, the clamping device and the sleeve are coaxial with the X-rays; an axis of the first transverse connecting rod, an axis of the longitudinal connecting rod and an axis of the second transverse connecting rod are provided in a same plane.

4. The auxiliary device according to claim 1, wherein a longitudinal section of the inner ring of the first bearing is convex, the outer ring is provided at two shoulder portions of the inner ring, the slip ring is fixed with the inner ring through a bolt, the drive mechanism which is set on the external surface of the outer ring comprises a drive motor and a timing belt, the drive motor is connected with the outer ring through a motor connection plate, a driving gear is set on the drive motor, a driven gear is set on an external surface of the inner ring, and the timing belt is provided between the driving gear and the driven gear.

5. The auxiliary device according to claim 4, wherein the slip ring is fixed with the inner ring through a bolt, the drive mechanism which is set on the external surface of the outer ring comprises a drive motor, a driving gear is set on the drive motor, a driven gear is set on an external surface of the inner ring, the driving gear is engaged with the driven gear for driving the driven gear to rotate.

6. The auxiliary device according to claim 1, wherein the swing device comprises a swing motor, a swing reducer, a swing shaft and a leather belt, wherein an output shaft of the swing motor is connected with an input shaft of the swing reducer through gear transmission, a driving pulley is provided on an output shaft of the swing reducer, the swing shaft is horizontally set on an upper end of the support device through a swing bearing, a driven pulley is provided at an outer end of the swing shaft, an inner end of the swing shaft is connected with the outer ring through a connection block, the leather belt is provided between the driving pulley and the driven pulley.

7. The auxiliary device according to claim 6, wherein the swing device comprises a swing motor, a swing reducer, a swing shaft, a driving swing gear and a driven swing gear, wherein an output shaft of the swing motor is connected with an input shaft of the swing reducer through gear transmission, the driving swing gear is provided on an output shaft of the swing reducer, the swing shaft is horizontally set on an upper end of the support device through a swing bearing, the driven swing gear is provided at an outer end of the swing shaft, an inner end of the swing shaft is connected with the outer ring through a connection block, the driving swing gear is engaged with the driven swing gear for driving the driven swing gear to rotate.

8. The auxiliary device according to claim 1, wherein the rotating device comprises a tray, wherein the tray has a tray hole in a center thereof, a rotating motor and a rotating reducer are located under the tray, a rotating disk is located on the tray, the rotating reducer is connected with the rotating motor, an output shaft of the rotating reducer passes through the tray hole and is connected with the rotating disk, so that the rotating motor is able to drive the rotating disk to rotate;

the support device has a U-shaped structure, an upper portion of the rotating disk is connected with a lower portion of a transverse plate of the U-shaped structure, two rotating sliders are respectively provided at left and right sides of the transverse plate, an arc-shaped slide rail is provided on an upper surface of the tray, the rotating sliders are locked on the arc-shaped slide rail, so that with a rotation of the rotating disk, the transverse plate is driven to rotate, so as to drive the rotating sliders to slide along the arc-shaped slide rail.

9. The auxiliary device according to claim 1, wherein the lifting device comprises a lifting screw and a lifting motor, wherein an upper end of the lifting screw is connected with a lower surface of the tray, a lower end of the lifting screw is provided on the lifting motor, the lifting motor is provided within the skid platform unit, so that the lifting motor rotates to drive the lifting screw to move up and down, so as to further drive the tray to move up and down.

10. The auxiliary device according to claim 1, wherein the skid platform unit comprises an outside skid platform, a middle skid platform and an inside skid platform, wherein the middle skid platform is sleeved within the outside skid platform and is able to move left and right along the outside skid platform, the inside skid platform is sleeved within the middle skid platform and is able to move back and forth along the middle skid platform, the lifting screw and the lifting motor are provided within the inside skid platform;

- a first slide rail, a first lead screw, a first lead screw motor and a first bracket are provided on the outside skid platform; the first lead screw motor is provided on the first bracket, one end of the first lead screw is connected with an output shaft of the first lead screw motor, and another end of the first lead screw passes through the first bracket and is provided on the middle skid platform;
- a first slider fitted with the first slide rail is provided at an outer side of the middle skid platform; a second slide rail, a second lead screw, a second lead screw motor and a second bracket are provided at an inner side of the middle skid platform; the second lead screw motor is provided on the second bracket, one end of the second lead screw is connected with an output shaft of the second lead screw motor, and another end of the second lead screw passes through the second bracket and is provided on the inside skid platform;
- a second slider fitted with the second slide rail is provided at an outer side of the inside skid platform, an inner side of the inside skid platform has a vertical round passage as a lifting slideway, and the lifting screw is sleeved within the lifting slideway.

* * * * *